(12) United States Patent
Laubacher et al.

(10) Patent No.: US 7,355,401 B2
(45) Date of Patent: Apr. 8, 2008

(54) USE OF TWO OR MORE SENSORS TO DETECT DIFFERENT NUCLEAR QUADRUPOLE RESONANCE SIGNALS OF A TARGET COMPOUND

(75) Inventors: Daniel B. Laubacher, Wilmington, DE (US); James D. McCambridge, Swarthmore, PA (US); Charles Wilker, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/051,786

(22) Filed: Feb. 4, 2005

(65) Prior Publication Data

US 2005/0206382 A1    Sep. 22, 2005

Related U.S. Application Data

(60) Provisional application No. 60/541,784, filed on Feb. 4, 2004.

(51) Int. Cl.
    *G01V 3/00* (2006.01)
(52) U.S. Cl. ...................................... 324/300; 324/311
(58) Field of Classification Search ................ 324/311, 324/300, 307, 314
    See application file for complete search history.

(56) References Cited

U.S. PATENT DOCUMENTS

| | | | |
|---|---|---|---|
| 3,373,348 A | 3/1968 | Vanier et al. | |
| 3,764,892 A | 10/1973 | Rollwitz | |
| 4,027,768 A | 6/1977 | Riessen | |
| 4,072,768 A | 2/1978 | Fraser et al. | |
| 4,514,691 A | 4/1985 | De Los Santos et al. | |
| 5,036,279 A | 7/1991 | Jonsen | |
| 5,135,908 A | 8/1992 | Yang et al. | |
| 5,206,592 A | 4/1993 | Buess et al. | |
| 5,233,300 A | 8/1993 | Buess et al. | |
| 5,258,710 A | 11/1993 | Black et al. | |
| 5,262,394 A | 11/1993 | Wu et al. | |
| 5,276,398 A | 1/1994 | Withers et al. | |
| 5,351,007 A | 9/1994 | Withers et al. | |
| 5,418,213 A | 5/1995 | Tanaka et al. | |
| 5,457,385 A | 10/1995 | Sydney et al. | |
| 5,583,437 A | 12/1996 | Smith et al. | |
| 5,585,723 A | 12/1996 | Withers | |
| 5,592,083 A | 1/1997 | Magnuson et al. | |
| 5,594,338 A | 1/1997 | Magnuson | |
| 5,656,937 A | 8/1997 | Cantor | |

(Continued)

FOREIGN PATENT DOCUMENTS

EP    0 426 851    5/1991

(Continued)

OTHER PUBLICATIONS

He, D.F. et al., "Metal detector based on high-Tc RF SQUID", Physica C 378-381 b(2002) pp. 1404-1407.

(Continued)

*Primary Examiner*—Louis M. Arana

(57) ABSTRACT

The use of two or more sensors tuned to at least two different nuclear quadrupole resonance frequencies of a target compound to detect the different nuclear quadrupole resonance signals greatly reduces the chance of misidentification, and thereby improves nuclear quadrupole resonance detection system performance.

10 Claims, 1 Drawing Sheet

U.S. PATENT DOCUMENTS

| | | | |
|---|---|---|---|
| 5,661,400 A | 8/1997 | Plies et al. |
| 5,750,473 A | 5/1998 | Shen |
| 5,751,146 A | 5/1998 | Hrovat |
| 5,804,967 A | 9/1998 | Miller et al. |
| 5,814,987 A | 9/1998 | Smith et al. |
| 5,814,989 A | 9/1998 | Smith et al. |
| 5,814,992 A | 9/1998 | Busse-Gravitz et al. |
| 5,872,080 A | 2/1999 | Arendt et al. |
| 5,952,269 A | 9/1999 | Ma et al. |
| 5,973,495 A | 10/1999 | Mansfield |
| 5,986,455 A | 11/1999 | Magnuson |
| 5,999,000 A | 12/1999 | Srinivasan |
| 6,025,719 A | 2/2000 | Anderson |
| 6,054,856 A | 4/2000 | Garroway et al. |
| 6,088,423 A | 7/2000 | Krug et al. |
| 6,091,240 A | 7/2000 | Smith et al. |
| 6,104,190 A | 8/2000 | Buess et al. |
| 6,108,569 A | 8/2000 | Shen |
| 6,150,816 A | 11/2000 | Srinivasan |
| 6,166,541 A | 12/2000 | Smith et al. |
| 6,169,399 B1 | 1/2001 | Zhang et al. |
| 6,194,898 B1 | 2/2001 | Magnuson et al. |
| 6,201,392 B1 | 3/2001 | Anderson et al. |
| 6,218,943 B1 | 4/2001 | Ellenbogen |
| 6,242,918 B1 | 6/2001 | Miller et al. |
| 6,291,994 B1 | 9/2001 | Kim et al. |
| 6,335,622 B1 | 1/2002 | James et al. |
| 6,370,404 B1 | 4/2002 | Shen |
| D459,245 S | 6/2002 | Power |
| 6,420,872 B1 | 7/2002 | Garroway et al. |
| 6,486,838 B1 | 11/2002 | Smith et al. |
| 6,538,445 B2 | 3/2003 | James et al. |
| 6,541,966 B1 | 4/2003 | Keene |
| 6,556,013 B2 | 4/2003 | Withers |
| 6,566,873 B1 | 5/2003 | Smith et al. |
| 6,590,394 B2 | 7/2003 | Wong et al. |
| 6,617,591 B1 | 9/2003 | Simonson et al. |
| 6,653,917 B2 | 11/2003 | Kang et al. |
| 6,751,489 B2 | 6/2004 | Shen |
| 6,751,847 B1 | 6/2004 | Brey et al. |
| 6,777,937 B1 | 8/2004 | Miller et al. |
| 6,819,109 B2 | 11/2004 | Sowers et al. |
| 6,847,208 B1 | 1/2005 | Crowley et al. |
| 6,952,163 B2 | 10/2005 | Huey et al. |
| 6,956,476 B2 | 10/2005 | Buess et al. |
| 6,958,608 B2 | 10/2005 | Takagi et al. |
| 7,049,814 B2 | 5/2006 | Mann |
| 7,106,058 B2 | 9/2006 | Wilker et al. |
| 2002/0068682 A1 | 6/2002 | Shen |
| 2002/0153891 A1 | 10/2002 | Smith et al. |
| 2002/0156362 A1 | 10/2002 | Bock et al. |
| 2002/0169374 A1 | 11/2002 | Jevtic |
| 2002/0190715 A1 | 12/2002 | Marek |
| 2003/0020553 A1 | 1/2003 | Gao et al. |
| 2003/0062896 A1 | 4/2003 | Wong et al. |
| 2003/0071619 A1 | 4/2003 | Sauer et al. |
| 2003/0119677 A1 | 6/2003 | Qiyan et al. |
| 2003/0136920 A1 | 7/2003 | Flores et al. |
| 2004/0124840 A1 | 7/2004 | Reykowski |
| 2004/0222790 A1 | 11/2004 | Karmi et al. |
| 2004/0251902 A1 | 12/2004 | Takagi et al. |
| 2005/0104593 A1 | 5/2005 | Laubacher et al. |
| 2005/0122109 A1 | 6/2005 | Wilker et al. |
| 2005/0140371 A1 | 6/2005 | Alvarez et al. |
| 2005/0146331 A1 | 7/2005 | Flexman et al. |
| 2005/0206382 A1 | 9/2005 | Laubacher et al. |
| 2005/0248345 A1 | 11/2005 | Alvarez |
| 2005/0258831 A1 | 11/2005 | Alvarez |
| 2005/0264289 A1 | 12/2005 | Alvarez |
| 2005/0270028 A1* | 12/2005 | Alvarez et al. ............ 324/311 |
| 2006/0012371 A1 | 1/2006 | Laubacher et al. |
| 2006/0038563 A1 | 2/2006 | Cisholm et al. |
| 2006/0082368 A1 | 4/2006 | McCambridge |
| 2006/0119360 A1 | 6/2006 | Yamamoto et al. |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269108 | 10/1993 |
| JP | 07 265278 | 10/1995 |
| WO | WO 92/17793 | 10/1992 |
| WO | WO 92/17794 | 10/1992 |
| WO | WO 92/19978 | 11/1992 |
| WO | WO 92/21989 | 12/1992 |
| WO | WO 94/05022 | 3/1994 |
| WO | WO 95/34096 | 12/1995 |
| WO | WO 96/39636 | 12/1996 |
| WO | WO 96/39638 | 12/1996 |
| WO | WO 98/37438 | 8/1998 |
| WO | WO 98/54590 | 12/1998 |
| WO | WO 99/45409 | 9/1999 |
| WO | WO 99/50689 | 10/1999 |
| WO | WO 00/70356 | 11/2000 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 04/001454 A | 12/2003 |
| WO | WO 04/102596 | 11/2004 |
| WO | WO 05/059582 A1 | 6/2005 |

OTHER PUBLICATIONS

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

Miller, et al., "Performance of a High-Termperature Superconducting Probe for In Vivo Microscopy at 2.0 T", Magnetic Resonance in Medicine, (1999) pp. 72-79, vol. 41.

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Reivew, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada (Sep. 14-17, 1993) Sep. 14, 1993 XP 010118071.

W. A. Edelstein et al., A signal-to-noise calibration procedure for NMR imaging systems, Medical Physics, vol. 11 (2) Mar./Apr. 1984, pp. 180-185.

T. Hirschfeld, "Short Range Remote Nqr Measurements", Journal of Molecular Structure, (1980) pp. 63-77, vol. 58, Elsevier Scientific Publishing Company, Amsterdam.

Garroway, et al., "Remote Sensing by Nuclear Quadrupole Resonance", IEEE Transactions on Geoscience and Remote Sensing, Jun. 2001, pp. 1108-1118, vol. 39, No. 6.

Garroway, et al., "Narcotics and explosives detection by N pure NQR", SPIE, (1993) pp. 318-327, vol. 2092.

Bendall, et al., "Elimination of Coupling between Cylindrical Transmit Coils and Surface-Receive Coils for in Vivo NMR" Magnetic Resonance in Medicine v3 p. 157-163, 1986.

Black, et al., "A High-Temperature Superconducting Receiver For Nuclear Magnetic Resonance Microscopy", Science, vol. 259, pp. 793-795 Feb. 5, 1993.

Black, et al., "Performance Of A High-Temperature Superconducting Resonator For High-Field Imaging", Journal Of Magnetic Resonance, pp. 74-80 (1995).

Colton, et. al., "Making the World a Safer Place", Science, v.299, i.5611, Pgd. 1324-1325, Feb. 2006.

Fisher, et al., "A Versatile Computer-Controlled Pulsed Nuclear Quadrupole Resonance Spectrometer", Review of Scientific Instruments, v70, No.12, p. 4678, Dec. 1999.

Hill, "Improved Sensitivity of NMR Spectroscopy Probes By Use Of High-Temperature Superconductive Detection Coils", IEEE Transactions On Applied Superconductivity, vol. 7, pp. 3750-3753, Jun. 1997.

Roemer, et. al., "The NMR Phased Array", Magnetic Resonance in Medicine 16, pp. 192-225, 1990.

Withers, et al., "Thin-Film HTD Probe Coils For Magnetic-Resonance Imaging", IEEE Transactions On Applied Superconductivity, vol. 3, pp. 2450-2453, Mar. 1993.

Landers, et al., "Electronic Effects and Molecular Motion in β-Octahydro-1,3,5,7-tetranitro-1,3,5,7-tetrazocine Bases on $^{14}$N Nuclear Quadrupole Resonance Spectroscopy", American Chemical Society, J. Phys. Chem., 85, pp. 2618-2623, 1981.

Karpowicz, et. al., "Librational Motion of Hexahydro-1,3,5-trinitros-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87, pp. 2109-2112, 1983.

Volpicelli, et. al., "Locked rf Spectrometer for Nuclear Quadrupole Resonance", The Review of Scientific Instruments, v.25, No. 2, pp. 150-153, Feb. 1965.

Benedek, et. al., "Precise Nuclear Resonance Thermometer", The Review of Scientific Instruments, v.28, No. 2, pp. 92-95, Feb. 1957.

Ernst, "Magnetic Resonance with Stochastic Excitation", Journal of Magnetic Resonance 3, pp. 10-27, 1970.

Klainer, et. al., "Fourier Transform Nuclear Quadrupole Resonance Spectroscopy", Fourier, Hadamard, and Hilbert Transforms in Chemistry, pp. 147-182, 1982.

\* cited by examiner

USE OF TWO OR MORE SENSORS TO DETECT DIFFERENT NUCLEAR QUADRUPOLE RESONANCE SIGNALS OF A TARGET COMPOUND

This application claims the benefit of U.S. Provisional Application No. 60/541,784, filed Feb. 4, 2004, which is incorporated in its entirety as a part hereof for all purposes.

FIELD OF THE INVENTION

This invention relates to a nuclear quadrupole resonance detection system and to the use therein of two or more sensors. The sensors are tuned to at least two different nuclear quadrupole resonance frequencies of a target compound to detect the different nuclear quadrupole resonance signals, and thereby provide improved nuclear quadrupole resonance detection system performance.

BACKGROUND OF THE INVENTION

The use of nuclear quadrupole resonance (NQR) as a means of detecting explosives and other contraband has been recognized for some time. See e.g. T. Hirshfield et al, *J. Molec. Struct.* 58, 63 (1980); A. N. Garroway et al, *Proc. SPIE* 2092, 318 (1993); and A. N. Garroway et al, *IEEE Trans. on Geoscience and Remote Sensing* 39, 1108 (2001). NQR provides some distinct advantages over other detection methods. NQR requires no external magnet such as required by nuclear magnetic resonance. NQR is sensitive to the compounds of interest, i.e. there is a specificity of the NQR frequencies.

One technique for measuring NQR in a sample is to place the sample within a solenoid coil that surrounds the sample. The coil provides a radio frequency (RF) magnetic field that excites the quadrupole nuclei in the sample and results in their producing their characteristic resonance signals. This is the typical apparatus configuration that might be used for scanning mail, baggage or luggage.

There is also a need for a NQR detector that permits detection of NQR signals from a source outside the detector, e.g. a wand detector, that could be passed over persons or containers as is done with existing metal detectors. Problems associated with such detectors using conventional systems are the decrease in detectability with distance from the detector coil, and the associated equipment needed to operate the system.

A detection system can have one or more coils that both transmit and receive, or it can have separate coils that only transmit and only receive. A transmit, or transmit and receive, coil of an NQR detection system provides a radio frequency (RF) magnetic field that excites the quadrupole nuclei in the sample and results in their producing their characteristic resonance signals that the coil receives. The NQR signals have low intensity and short duration. The transmit, receive, or transmit and receive, coil preferably has a high quality factor (Q). The transmit, receive, or transmit and receive, coil has typically been a copper coil and therefore has a Q of about $10^2$.

It can be advantageous to use a transmit, receive, or transmit and receive, coil made of a high temperature superconductor (HTS) rather than copper since the HTS self-resonant coil has a Q of the order of $10^3$-$10^6$. The large Q of the HTS self-resonant coil produces large magnetic field strengths during the RF transmit pulse and does so at lower RF power levels. This dramatically reduces the amount of transmitted power required to produce NQR signals for detection, and thereby reduces the size of the RF power supply sufficiently so that it can be run on portable batteries.

The large Q of the HTS self-resonant coil also plays an important role during the receive time. In view of the low intensity NQR signal, it is important to have a signal-to-noise ratio (S/N) as large as possible. The signal-to-noise ratio is proportional to the square root of Q so that the use of the HTS self-resonant coil results in an increase in S/N by a factor of 10-100 over that of the copper system.

These advantages during both the transmit and the receive times enable a detector configuration that is small and portable. In particular, the use of a high temperature superconductor sensor receive coil prepared from a high temperature superconductor material, provides a distinct advantage over the use of an ordinary conductor coil.

One goal in using NQR for the detection of contraband is to minimize the number of erroneous results. A target compound that is an NQR source has a plurality of signature NQR frequencies, i.e. a set of NQR frequencies that is specific to that compound. Any one of these frequencies may overlap the NQR line of another compound. With a sensor tuned to such a frequency there can be false-positive identifications as a result of the intentional or inadvertent presence of the other compound.

An object of the present invention is to provide a NQR detection system with improved performance with respect to misidentification of an NQR source.

BRIEF DESCRIPTION OF THE DRAWINGS

The invention will be more fully understood from the following detailed description, taken in connection with the accompanying drawing, which form a part of this application and in which the sole FIGURE is a diagrammatic representation of an apparatus in accordance with the present invention and used to practice the method of the present invention.

SUMMARY OF THE INVENTION

Figure 1:
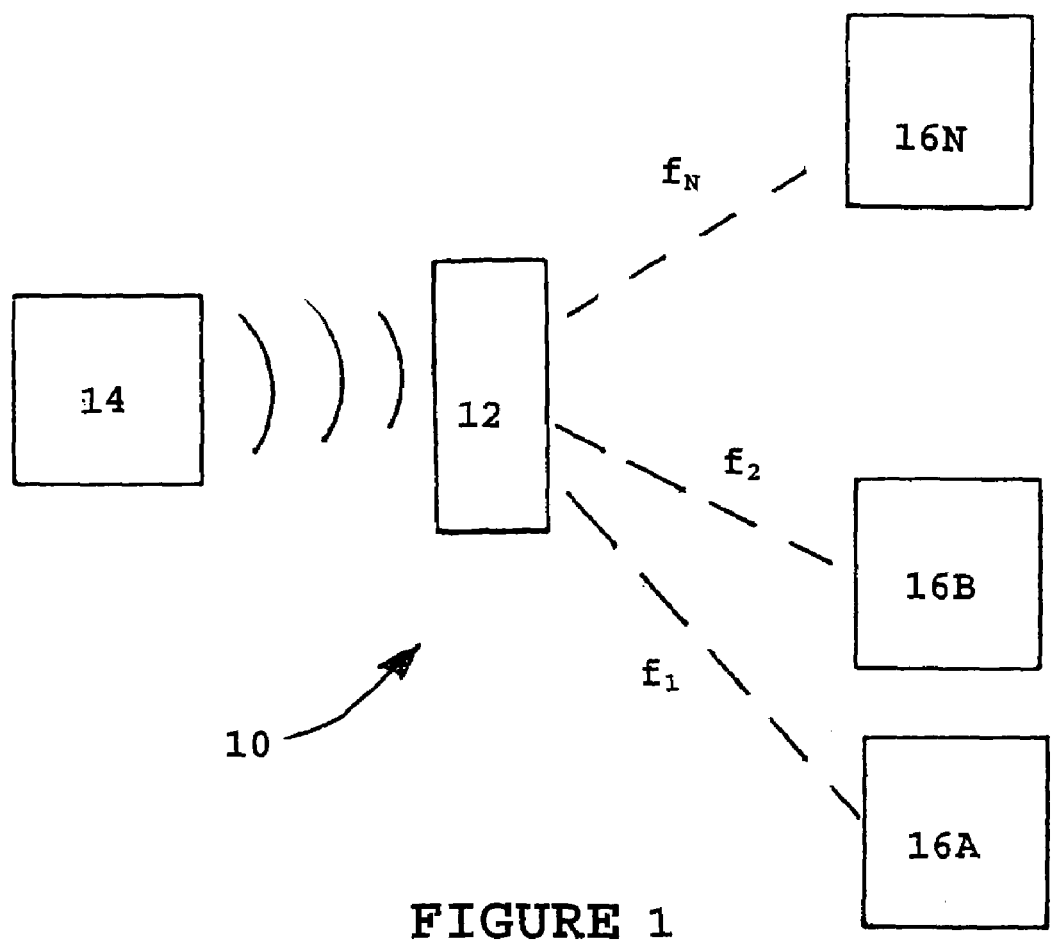

One embodiment of this invention is a method of detecting nuclear quadrupole resonance in a target compound by applying a radio frequency magnetic field to the target compound, and providing two or more sensors tuned to at least two different nuclear quadrupole resonance frequencies of the target compound to detect the different nuclear quadrupole resonance signals thereof.

Another embodiment of this invention is a method of detecting nuclear quadrupole resonance in a target compound by applying a radio frequency magnetic field to the target compound, and providing N sensors tuned to M different nuclear quadrupole resonance frequencies of the target compound to detect the M different nuclear quadrupole resonance signals thereof, wherein $N \geq 2$ and $2 \leq M \leq N$.

A further embodiment of this invention is a nuclear quadrupole resonance detection system that includes two or more sensors tuned to at least two different nuclear quadrupole resonance frequencies of a target compound, wherein the sensors detect the different nuclear quadrupole resonance signals characteristic of the target compound.

Yet another embodiment of this invention is a nuclear quadrupole resonance detection system that includes N sensors tuned to M different nuclear quadrupole resonance frequencies of a target compound, wherein the N sensors detect the M different nuclear quadrupole resonance signals, and wherein $N \geq 2$ and $2 \leq M \leq N$.

In the drawing reference character 10 denotes an NQR detection system in accordance with the present invention and used to practice the method of the present invention. Reference character 12 denotes an object containing a target compound that is interrogated using the system 10. Reference character 14 denotes one shielded-loop high temperature superconductor resonator coil for applying a radio frequency magnetic field to the target compound. The energy spectrum of the resonator coil 14 is sufficiently broad to produce a number of different nuclear quadrupole resonance signals from the target compound. The frequency of the NQR responses are indicated by reference character $f_1, f_2, \ldots f_N$. Reference characters 16A, 16B, ... 16N denote N number of sensors. Each sensor is implemented using a high temperature superconductor self-resonant planar coil. Each sensor is a high temperature superconductor self-resonant planar coil operative solely to detect nuclear quadrupole resonance signals. Each sensor is tuned to a different nuclear quadrupole resonance frequency $f_1, f_2, \ldots f_N$ emanating from the target compound.

Preferably, the two or more sensors are used solely for sensing, i.e. receiving, the NQR signals, and one or more separate coils are used as the transmit, i.e. excitation, coils to provide the RF magnetic field that excites the quadrupole nuclei in the target compound to be scanned. Preferably, each sensor is a high temperature superconductor coil. More preferably, each sensor is comprised of a high temperature superconductor self-resonant planar coil, or is comprised of two or more coupled high temperature superconductor self-resonant planar coils.

This invention for improving the reliability of the identification of a target compound, and thereby improving the performance of a nuclear quadrupole resonance detection system, is especially important when the nuclear quadrupole resonance detection system is used for detecting the nuclear quadrupole resonance of explosives, drugs and other contraband.

DETAILED DESCRIPTION OF THE PREFERRED EMBODIMENTS

This invention provides a method of nuclear quadrupole detection in which the false alarm rate is improved by requiring confirmation of the presence of at least two different NQR frequencies of a target compound. This invention also provides an NQR detection system that can accomplish this improved performance.

In this invention, two or more sensors tuned to at least two different nuclear quadrupole resonance frequencies of a target compound are used to detect the different nuclear quadrupole resonance signals emitted by the compound. That is, this invention uses N sensors, wherein $N \geq 2$. These N sensors are tuned to M different nuclear quadrupole resonance frequencies, wherein $2 \leq M \leq N$. For example, if 3 sensors were used, 2 sensors could be tuned to one nuclear quadrupole resonance frequency, and the other sensor could be tuned to a different nuclear quadrupole resonance frequency of the same compound. Alternatively, the 3 sensors could be tuned to 3 different nuclear quadrupole resonance frequencies of the same compound.

While one of the NQR frequencies of the target compound may overlap an NQR line of another compound, it is unlikely that two or more NQR frequencies of the target compound would both or all overlap NQR lines of the other compound. Therefore, the use of two or more sensors tuned to at least two different nuclear quadrupole resonance frequencies of the target compound to detect the different nuclear quadrupole resonance signals, and thereby make an identification of the target compound, greatly reduces the probability of a false-positive identification.

A "sensor" as used in this invention is a receive device, such as a receive coil, and the sensors used to detect nuclear quadrupole resonance in a target compound will typically be used as receive coils only. In certain embodiments, it may be possible to use them as transmit and receive coils, but, preferably, separate coils are used to transmit the RF signal, and the sensors (as their name implies) are used solely as receive coils.

Preferably, the two or more sensors are high temperature superconductor (HTS) coils. A high temperature superconductor coil is preferably in the form of a self-resonant planar coil, i.e. a surface coil, with a coil configuration of HTS on one or both sides of a substrate. High temperature superconductors are those that superconduct above 77K. The high temperature superconductors used to form the HTS self-resonant coil are preferably selected from the group consisting of $YBa_2Cu_3O_7$, $Tl_2Ba_2CaCu_2O_8$, $TlBa_2Ca_2Cu_3O_9$, $(TlPb)Sr_2CaCu_2O_7$ and $(TlPb)Sr_2Ca_2Cu_3O_9$. Most preferably, the high temperature superconductor is $YBa_2Cu_3O_7$ or $Tl_2Ba_2CaCu_2O_8$.

An HTS self-resonant coil can be formed by various known techniques. Preferably, a planar coil is formed by first depositing HTS layers on both sides of a single crystal substrate. In a preferred technique for forming a $Tl_2Ba_2CaCu_2O_8$ coil, the HTS layers are formed directly on a single crystal $LaAlO_3$ substrate or on a $CeO_2$ buffer layer on a single crystal sapphire ($Al_2O_3$) substrate. An amorphous precursor layer of Ba:Ca:Cu oxide about 500 nm thick and with a stoichiometry of about 2:1:2 is deposited by off-axis magnetron sputtering from a Ba:Ca:Cu oxide target. The precursor film is then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_8$ phase.

The sample is then coated with photoresist on both sides and baked. A coil design mask is prepared. The design mask is then centered on the photoresist covering the $Tl_2Ba_2CaCu_2O_8$ film on the front side of the substrate and exposed to ultraviolet light. If the coil is to have the same HTS pattern on both sides of the substrate, the design mask is then centered on the photoresist covering the $Tl_2Ba_2CaCu_2O_8$ film on the back side of the substrate and exposed to ultraviolet light. The resist is then developed on both sides of the substrate and the portion of the $Tl_2Ba_2CaCu_2O_8$ film exposed when the resist is developed is etched away by argon beam etching. The remaining photoresist layer is then removed by an oxygen plasma. The result is the desired HTS coil. If two coupled high temperature superconductor self-resonant coils are to be used as the sensor coil, a second coil can be produced using the same technique.

HTS self-resonant coils have high Q's and relatively small size. The use of HTS self-resonant coils as sensors makes the use of an array of two or more sensors in the instant invention especially attractive. If one or more HTS coils are used, provision must also be made for cooling the HTS to liquid nitrogen temperature.

It is often advantageous to be able to fine-tune the resonance frequency of the sensor. One means for accomplishing such tuning is to use two or more coupled high temperature superconductor self-resonant coils. The resonance frequency of the fundamental symmetric mode of the two or more coupled high temperature superconductor self-resonant coils can be varied by mechanically displacing the coils with respect to one another, and these coupled coils may serve as the HTS sensor. Preferably, the two or more coils are planar, i.e. surface, coils. Each planar coil has a HTS coil configuration on only one side of the substrate, or has essentially identical HTS coil configurations on both sides of the substrate. Most preferably, the HTS sensor coils are each comprised of a high temperature superconductor self-resonant planar coil or two or more coupled high temperature superconductor self-resonant planar coils.

As indicated above, when two or more coupled high temperature superconductor self-resonant coils are used as a sensor, the resonance frequency of the fundamental symmetric mode of the two or more coupled high temperature self-resonant coils can be varied by mechanically displacing one coil with respect to the other. Means for tuning the resonance frequency of the sensor to a specified nuclear quadrupole resonance frequency thus includes actuators to mechanically displace the coils as described above.

Alternatively, for a sensor comprised of a high temperature superconductor self-resonant coil or two coupled high temperature superconductor self-resonant coils, means for tuning the resonance frequency of the sensor to a specified nuclear quadrupole resonance frequency may also include a circuit. The circuit may be comprised of a single loop or coil to inductively couple the circuit to the high temperature superconductor self-resonant sensor, a reactance in series with the single loop or coil, and means to connect and disconnect the reactance to and from the single loop or coil. In essence, the tuning circuit is resonated which causes a mode split by coupling to the self-resonant high temperature superconductor sensor.

The single loop or coil can be made of a regular conductor such as copper or a high temperature superconductor. The reactance can be an inductance, capacitance or combination of both. The means to connect and disconnect the reactance to and from the single loop or coil may include at least one mechanical switch or electrical switch such as a diode. Preferably, the reactance can be varied so that the resonance frequency can be adjusted to more than one frequency. A variable reactance may be provided in the form of two or more capacitors in parallel, each of which can be individually connected to or disconnected from the single loop or coil. Alternatively, a variable reactance may comprise two or more inductors in series, each of which can be individually connected to or disconnected from the single loop or coil by a mechanical or electrical switch that can short-circuit the inductor, and thereby essentially remove it from the circuit.

The transmit coils used in this invention can be made of copper, silver, aluminum or a high temperature superconductor. A copper, silver or aluminum coil is preferably in the form of a shielded-loop resonator (SLR) coil. SLR's have been developed to eliminate the detuning effect of the electrical interaction between the coil and the surrounding material. Preferably, one or more SLR copper transmit coils are used to apply the RF signal to the sample.

More than one transmit coil may be needed to apply the RF signal necessary to excite the quadrupole nuclei and produce the various different nuclear quadrupole resonance signals characteristic of the target compound. Provision must be made for a power supply to supply power for transmitting the RF pulse.

While the discussion herein is presented primarily in terms of the use of a coil as the transmit, receive or transmit and receive device, this invention is not limited thereto, and is applicable to transmit, receive and transmit and receive devices that may have a configuration other than that of a coil.

Where an apparatus or method of this invention is stated or described as comprising, including, containing, having, being composed of or being constituted by certain components or steps, it is to be understood, unless the statement or description explicitly provides to the contrary, that one or more components or steps other than those explicitly stated or described may be present in the apparatus or method. In an alternative embodiment, however, the apparatus or method of this invention may be stated or described as consisting essentially of certain components or steps, in which embodiment components or steps that would materially alter the principle of operation or the distinguishing characteristics of the apparatus or method would not be present therein. In a further alternative embodiment, the apparatus or method of this invention may be stated or described as consisting of certain components or steps, in which embodiment components or steps other than those as stated would not be present therein.

Where the indefinite article "a" or "an" is used with respect to a statement or description of the presence of a component in an apparatus, or a step in a method, of this invention, it is to be understood, unless the statement or description explicitly provides to the contrary, that the use of such indefinite article does not limit the presence of the component in the apparatus, or of the step in the method, to one in number.

What is claimed is:

1. A method of detecting nuclear quadrupole resonance in a target compound comprising the steps of:
    (a) applying a radio frequency magnetic field to the target compound using only one shielded-loop resonator coil thereby to produce at least two different nuclear quadrupole resonance signals from the target compound; and
    (b) providing two or more high temperature superconductor self-resonant planar coil sensors, each sensor being operative solely to detect nuclear quadrupole resonance signals, each sensor being tuned to a different nuclear quadrupole resonance frequency of the target compound to detect the different nuclear quadrupole resonance signals thereof.

2. The method of claim 1 wherein the high temperature superconductor self-resonant planar coil sensors are $YBa_2Cu_3O_7$ or $Tl_2Ba_2CaCu_2O_8$ self-resonant planar coils, and wherein the shielded-loop resonator coil is a copper shielded-loop resonator coil.

3. A method of detecting nuclear quadrupole resonance in a target compound comprising the steps of:
    (a) applying a radio frequency magnetic field to the target compound using only one shielded-loop resonator coil thereby to produce at least M different nuclear quadrupole resonance signals from the target compound; and
    (b) providing N high temperature superconductor self-resonant planar coil sensors, each sensor being operative solely to detect nuclear quadrupole resonance signals, each sensor being tuned to one of the M different nuclear quadrupole resonance frequencies of the target compound to detect the M different nuclear quadrupole resonance signals thereof, wherein $N \geq 2$ and $2 \leq M \leq N$.

4. The method of claim 3, wherein the high temperature superconductor self-resonant planar coil sensors are $YBa_2Cu_3O_7$ or $Tl_2Ba_2CaCu_2O_8$ self-resonant planar coils, and wherein the shielded-loop resonator coil is a copper shielded-loop resonator coil.

5. The method of claim 1 or 3 wherein the target compound comprises explosives, drugs or other contraband.

6. A nuclear quadrupole resonance detection system comprising:
a single shielded-loop resonator coil operative to produce at least two different nuclear quadrupole resonance signals from a target compound; and
two or more high temperature superconductor self-resonant planar coil sensors, each sensor being operative solely to detect nuclear quadrupole resonance signals, each of the sensors being tuned to a different nuclear quadrupole resonance frequency of the target compound, wherein each of the sensors detects a different nuclear quadrupole resonance signal characteristic of the target compound.

7. The nuclear quadrupole resonance detection system of claim 6 wherein the high temperature superconductor self-resonant planar coil sensors are $YBa_2Cu_3O_7$ or $Tl_2Ba_2CaCu_2O_8$ self-resonant planar coils, and wherein the shielded-loop resonator coil is a copper shielded-loop resonator coil.

8. A nuclear quadrupole resonance detection system, comprising:
a single shielded-loop resonator coil operative to produce at least M different nuclear quadrupole resonance signals from a target compound; and
N high temperature superconductor self-resonant planar coil sensors each being operative solely to detect nuclear quadrupole resonance signals, each of the sensors being tuned to a different nuclear quadrupole resonance frequency of the target compound, wherein each of the N sensors detects a different one of the M different nuclear quadrupole resonance signals characteristic of the target compound, and wherein $N \geq 2$ and $2 \leq M \leq N$.

9. The nuclear quadrupole resonance detection system of claim 8 wherein the high temperature superconductor self-resonant planar coil sensors are $YBa_2Cu_3O_7$ or $Tl_2Ba_2CaCu_2O_8$ self-resonant planar coils, and wherein the shielded-loop resonator coil is a copper shielded-loop resonator coil.

10. The nuclear quadrupole resonance detection system of claim 6 or 8 wherein the target compound comprises explosives, drugs or other contraband.

* * * * *